(12) United States Patent
Sugioka

(10) Patent No.: US 9,574,993 B2
(45) Date of Patent: Feb. 21, 2017

(54) METHOD AND APPARATUS FOR ANALYZING THE CONCENTRATION OF MATERIALS IN SUSPENSION

(71) Applicant: SHIMADZU CORPORATION, Kyoto (JP)

(72) Inventor: Mikio Sugioka, Kameoka (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 14/489,244

(22) Filed: Sep. 17, 2014

(65) Prior Publication Data

US 2015/0369727 A1  Dec. 24, 2015

(30) Foreign Application Priority Data

Jun. 24, 2014 (JP) ................................ 2014-128971

(51) Int. Cl.
| | |
|---|---|
| *G01N 21/00* | (2006.01) |
| *G01N 21/31* | (2006.01) |
| *G01N 33/06* | (2006.01) |
| *G01N 33/14* | (2006.01) |
| G01N 21/3577 | (2014.01) |
| G01N 21/33 | (2006.01) |
| G01N 21/359 | (2014.01) |

(52) U.S. Cl.
CPC .............. *G01N 21/31* (2013.01); *G01N 33/06* (2013.01); *G01N 33/14* (2013.01); *G01N 21/33* (2013.01); *G01N 21/359* (2013.01); *G01N 21/3577* (2013.01); *G01N 2201/065* (2013.01)

(58) Field of Classification Search
CPC ........ G01N 21/47; G01N 21/00; G01N 33/00; G01N 30/00; G01N 27/00; H01J 49/00
USPC .......................... 356/336–339, 442–445, 437
See application file for complete search history.

(56) References Cited

U.S. PATENT DOCUMENTS

| | | | | |
|---|---|---|---|---|
| 4,482,245 A | * | 11/1984 | Makabe ................ | G01J 3/0251 356/244 |
| 5,164,597 A | * | 11/1992 | Lodder .................. | G01N 21/51 250/228 |
| 5,963,320 A | * | 10/1999 | Brooks .................... | G01J 3/06 356/310 |

(Continued)

OTHER PUBLICATIONS

U. Choka, "Sequential Measurement of the Components of Fresh Milk at the Time of Milking in Accordance with Near-Infrared Spectrometry," Hokkaido University Graduate School of Agriculture, Dept. of Life Resource Production, Life Production Engineering Course, Summary of Lectures for Presenting Theses for Master Degrees 1999 (Feb. 10, 2000).

*Primary Examiner* — Tarifur Chowdhury
*Assistant Examiner* — Isiaka Akanbi
(74) *Attorney, Agent, or Firm* — McDermott Will & Emery LLP

(57) ABSTRACT

A spectrometer equipped with an integrating sphere is used to measure a reflection spectrum from a suspension in a container when the suspension is irradiated with measurement light, of which wavelengths are selected from a wavelength range including near infrared. Reflection spectra of a number of types of standard samples, of which concentrations in the suspension are already known, are used to prepare a measurement model in accordance with an assay technique on the basis of a recursion. A concentration of the material in the suspension is found using the measurement model.

3 Claims, 11 Drawing Sheets

(56) References Cited

U.S. PATENT DOCUMENTS 8,749,791 B2 * 6/2014 Wimmer .................. G01J 1/04
356/236
2002/0183600 A1 * 12/2002 Tsenkova ............... G01N 21/31
600/310

* cited by examiner

METHOD AND APPARATUS FOR ANALYZING THE CONCENTRATION OF MATERIALS IN SUSPENSION

RELATED APPLICATIONS

This application claims the benefit of Japanese Application No. 2014-128971, filed on Jun. 24, 2014, the disclosures of which Applications are incorporated by reference herein.

BACKGROUND OF THE INVENTION

1. Field of the Invention

The present invention relates to a method and an apparatus for analyzing the concentration of materials in a suspension, and in particular to an analysis method and an analysis apparatus that are appropriate for analyzing the concentration of materials in a suspension with high turbidity, such as the analysis of the amount of lipids in milk, the concentration of vegetable juice, or the concentration of microscopic algae (so-called phytoflagellates) that float in water.

2. Description of Related Art

A Gerber method and a Babcock method have been used for the conventional measurement of the amount of lipids (butterfat) that are contained in milk or processed milk (they are generally referred to as milk in the present specification). According to both of these methods, concentrated sulfuric acid is added to milk so as to break the globule membrane that surrounds the milk fat, and then, droplets of milk fat that float in the concentrated sulfuric acid solution are collected through centrifugal separation, and thus, the volume is measured.

In place of these conventional techniques, a method for measuring the amount of lipids using near-infrared spectrometry has been put into practice. In accordance with this method for measurement using near-infrared spectrometry, milk is contained in a sample cell for measuring a liquid sample, and the sample cell is irradiated with light for measurement so that the transmitted light is detected to measure the absorption spectrum of the milk. After that, the amount of lipids in the milk to be measured is calculated from a measurement model that has been prepared in advance by measuring the absorption spectra of a number of types of milk, of which the amount of lipids are already known.

An online measuring method has also been proposed as a method for measuring the amount of lipids in milk using near-infrared spectrometry (see Non-Patent Document 1). In accordance with this technology, a sample chamber through which milk flows is irradiated with light from a halogen lamp so that spectrometry is carried out after guiding the diffuse transmission light to a spectrometer from milk through an optical fiber. The absorption spectrum of light from the milk that flows through the sample chamber is continuously measured so that the amount of lipids in the milk that flows through the sample chamber is sequentially measured online on the basis of the measurement model that has been prepared in advance.

PRIOR ART DOCUMENT

Non-Patent Document

Non-Patent Document 1: "Sequential Measurement of the Components of Fresh Milk at the Time of Milking in Accordance with Near-Infrared Spectrometry" by U Choka (Hokkaido University Graduate School of Agriculture, Department of Life Resource Production, Life Production Engineering Course, Summary of Lectures for Presenting Theses for Master Degrees in 1999, Feb. 10, 2000)

SUMMARY OF THE INVENTION

1. Problem to be Solved by the Invention

The Gerber method and the Babcock method for measuring the amount of lipids in milk have such problems that the measurement requires a long period of time and the use of sulfuric acid is dangerous.

In accordance with the technology for measuring the amount of lipids online, which is disclosed in Non-Patent Document 1, it is necessary to greatly change the structure of the conventional spectrometer to a completely different form. In addition, the technology disclosed in Non-Patent Document 1 provides a configuration where the light that has transmitted an object to be analyzed is guided to a spectrometer through an optical fiber for post-dispersive spectrometry, and therefore, precision in measurement cannot be expected.

Meanwhile, a method using a conventional spectrometer, with which a range from ultraviolet to near infrared can be measured, makes pre-dispersive spectrometry possible, and therefore, high precision in measurement can be expected. However, there are the following problems.

In the transmission measurement with an ultraviolet, visible, near-infrared spectrometer, light scatters due to the effects of the turbidity of milk, and thus, light does not reach the detector, which makes measurement difficult. In addition, the effects of absorption by light are tremendous, particularly in the near-infrared range (wavelength from approximately 900 nm to 2500 nm), which makes it difficult to gain a good spectrum in the transmission measurement (absorption measurement). Therefore, it is necessary to use a square cell, of which the optical path length is 2 mm or less, instead of a quartz cell, of which the optical path length is 10 mm, in order to suppress the absorption by water.

The same can be said in the cases where the concentration of particles that provide the turbidity to the liquid in a suspension with a relatively large turbidity other than milk, such as thick drinks, microscopic algae, and green vegetable juice, is measured with a spectrometer. Namely, suspensions with turbidity are diluted before being contained in a square cell so that the spectrum can be measured by means of the transmission measurement. In some cases where the turbidity is very low, measurement may be possible without the suspension being diluted. In suspensions having high turbidity, however, light scatters greatly, which prevents a sufficient amount of transmission light from reaching the detector, and thus makes measurement impossible. In such a case, it is necessary to carry out troublesome work, such as diluting the liquid to be measured. In addition, the same cell is prewashed and used repetitively for the measurement using a square cell, and therefore, it is necessary to wash the cell every time. In addition, such a problem arises that washing is difficult in the case where a cell, of which the optical path length is 2 mm or less, as described above is used, and thus, the concentration cannot be measured quickly and easily.

The present invention is provided in view of these situations, and an object thereof is to provide a method and an apparatus that make an easy and quick measurement of the concentration of materials in a suspension having high turbidity, such as the amount of lipids in milk, possible with high precision and without essentially changing the structure of the conventional spectrometer for pre-dispersive spectrometry.

2. Means for Solving Problem

The method for analyzing the concentration of a material in a suspension is characterized by including the steps of: using a spectrometer equipped with an integrating sphere; gaining a state where a sample container that contains a suspension to be analyzed faces the inside of the above-described integrating sphere through an opening of the integrating sphere; selecting wavelengths sequentially from a wavelength range including near infrared; irradiating the suspension in the above-described sample container with the measurement light through another opening of the above-described integrating sphere in the above-described state; detecting light reflected from the suspension with a detector provided in the integrating sphere so that a reflection spectrum is measured; and finding the concentration of the material in the above-described suspension to be analyzed from the results of the measurement of the reflection spectrum and a measurement model that has been prepared in accordance with an assay technique on the basis of a recursion using respective reflection spectra of a number of types of standard samples, of which the concentrations in the suspension are already known.

The present invention is provided as a result of diligent examination and research for the purpose of an easy and quick analysis of the concentration of materials in a suspension having high turbidity by solving the problems caused at the time of washing cells and the problems with the work of diluting a sample while maintaining the structure and precision of a multipurpose spectrometer of a pre-dispersive spectrometry type. The conclusions of the examination and research are that the concentration of materials in a suspension can be precisely measured by carrying out reflection measurement using the integrating sphere of the spectrometer.

That is to say, it is confirmed that the amount of lipids in milk, the concentration of vegetable juice, and the concentration of microscopic algae floating in water can be found with precision from a measurement model on the basis of a recursion by measuring the reflection spectrum of the suspension through reflection measurement using an integrating sphere.

The method according to the present invention utilizes such a relationship that the greater the amount of particles (suspended materials) in a suspension to be analyzed is, the higher the reflectance of measurement light from the vicinity of the liquid interface in the portion irradiated with the measurement light is due to an increase in the number of places from which the measurement light is reflected or scatters.

FIG. 1 conceptually shows the principle of the measurement in accordance with the method according to the present invention. In the case where the concentration of particles P in a suspension is high (A), measurement light L is mostly reflected from the particles P, most of which are in the vicinity of the liquid interface in the portion irradiated with the measurement light L, so as to be diffused to the outside of the container V. In the case where the concentration of particles P in a suspension is low (B), there are few particles P that are in the vicinity of the liquid interface in the portion irradiated with the measurement light L, and therefore, only a small amount of light is reflected from the particles P so as to be diffused to the outside of the container V, and thus, the measurement light mostly attenuates while proceeding through the suspension or is reflected from particles that are far away from the liquid interface so as to attenuate in the suspension before reaching the outside of the container V, and as a result, the intensity of reflected light is lower as compared to the case of (A).

When the reflected light that has diffused to the outside of the container V is integrated by an integrating sphere so as to be led to a detector so that the reflection spectrum of the suspension to be analyzed can be measured, the concentration of the materials in the suspension to be analyzed can be found from the results of the measurement and a measurement model that has been prepared in advance in accordance with an assay technique on the basis of a recursion using the reflectance of each reflection spectrum of a number of standard samples, of which the concentrations in the suspension are already known.

Though the measurement model may be based on either a simple linear regression that is an assay using the reflectance of one wavelength in the reflection spectrum or a multivariate analysis (multiple regression, PLS, or the like) that is an assay using the reflectance of a number of wavelengths, it has been confirmed that the measurement model on the basis of a multivariate analysis can allow a more precise analysis of the concentration in a suspension to be carried out.

In addition, the present invention relates to reflection measurement, and therefore, there are no cell (sample container) limitations due to the optical path length, unlike in the case of transmission measurement, and thus, no problem arises concerning the work of washing. In the case where a sample container is made disposable by using an inexpensive screw tube or the suspension is contained in a transparent container so as to be commercially available, it is possible to measure the suspension in such a product state as is. In addition, pre-dispersive spectrometry is carried out by using an integrating sphere, and therefore, it is not necessary to greatly modify the structure of the multipurpose spectrometer, and spectrum measurement with high precision is possible.

The apparatus for analyzing the concentration of a material in a suspension according to the present invention is an apparatus in which the analysis method according to the present invention is used, and the analysis apparatus is provided with: a light source for emitting white light in a wavelength range from ultraviolet to near infrared; a spectrometer for carrying out spectrometry on light from the light source; an integrating sphere having an opening for guiding measurement light through which measurement light, of which the wavelengths are sequentially selected by the spectrometer, is introduced, and an opening for setting a sample for reflection measurement provided along an optical path of the introduced measurement light; a detector that faces the inside of the integrating sphere and detects reflection light collected from the inner surface of the integrating sphere; a reflection spectrum calculating means for calculating the reflection spectrum of a sample on the basis of the output from the detector; a measurement model operating means for preparing a measurement model on the basis of an assay technique in accordance with a recursion using the respective reflection spectra of a number of standard samples, of which the concentrations in the suspension are already known; and a material concentration calculation means for calculating the concentration of a material in the suspension to be analyzed from the results of measurement of the reflection spectra of the suspension and the measurement model, and is characterized by further having outside the above-described integrating sphere a holding mechanism for fixing a container that contains a suspension to be analyzed to the above-described opening for setting a sample for reflection measurement in a constant positional relationship.

Meanwhile the analysis apparatus is characterized by further having outside the above-described integrating sphere a sample container supplying means for sequentially supplying containers that contain a suspension to be analyzed to the above-described opening for setting a sample for reflection measurement in sync with an operation of measuring a reflection spectrum in such a manner that the container is made to stop in the opening in a constant positional relationship.

The above-described analysis apparatus makes reflection measurement of a liquid sample possible while maintaining the basic structure of a multipurpose spectrometer. The analysis apparatus is provided with a holding mechanism for fixing a sample container to the opening of the integrating sphere for setting a sample for reflection measurement in a constant positional relationship, and thus makes it possible to increase the precision in reflection measurement of a liquid sample when the measurement is repeated.

Meanwhile, the invention allows sample containers to be sequentially supplied automatically in sync with an operation of measuring a reflection spectrum in such a manner that the sample container is made to stop in the opening of the integrating sphere for setting a sample for reflection measurement in a constant positional relationship, and thus makes precise measurement of a reflection spectrum possible online.

Effects of the Invention

According to the present invention, a reflection spectrum of a suspension is measured through reflection measurement using an integrating sphere for pre-dispersive spectrometry, and the concentration of the suspension is found by using a measurement model that has been prepared on the basis of an assay technique in accordance with a recursion, and therefore, the form of the sample container (cell) is not limited by the optical path length so that a sample container in any form can be used, as compared to a case where the concentration of a suspension is found from the absorption spectrum resulting from transmission measurement using a conventional spectrometer. For example, an inexpensive screw tube, which is disposable, can be used as a sample container at the time of measurement, or it is possible to use a suspension contained in a transparent container as a product, which can be distributed, for measurement as is. Thus, it is possible to quickly and easily measure the concentration of the materials in a suspension with high precision.

In addition, the analysis apparatus can be provided only by equipping a general purpose ultraviolet, visible, near-infrared spectrometer with an integrating sphere and by providing a mechanism for holding a sample container to the opening for setting a sample for reflection measurement or by providing a supplying means for supplying sample containers sequentially to the opening. Thus, it is not necessary to greatly modify the structure of the general purpose spectrometer, and therefore, the cost for the apparatus can be kept low and online measurement can be implemented.

DETAILED DESCRIPTION OF EMBODIMENTS

Figure 1A:
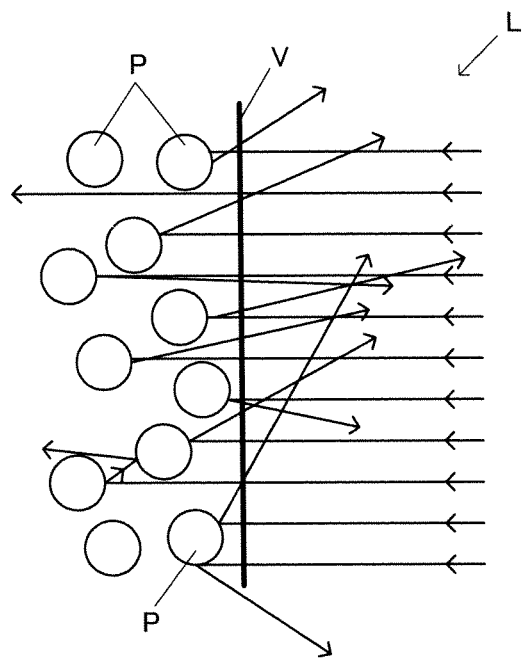
FIGS. 1A and 1B are conceptual diagrams illustrating the principle of the method according to the present invention.
Figure 1B:
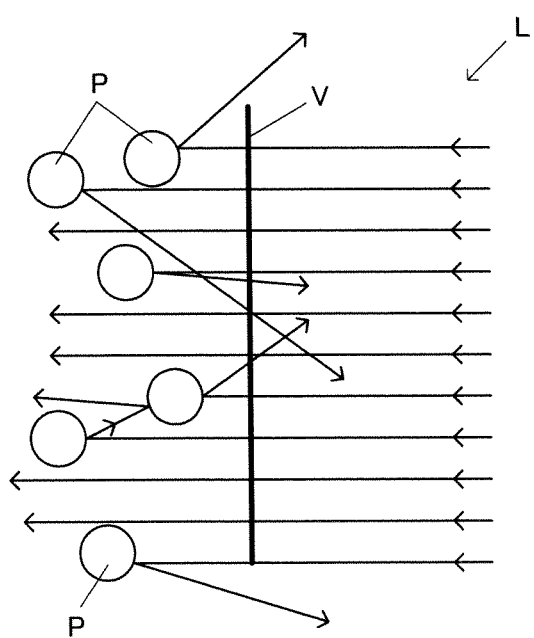
Figure 2:
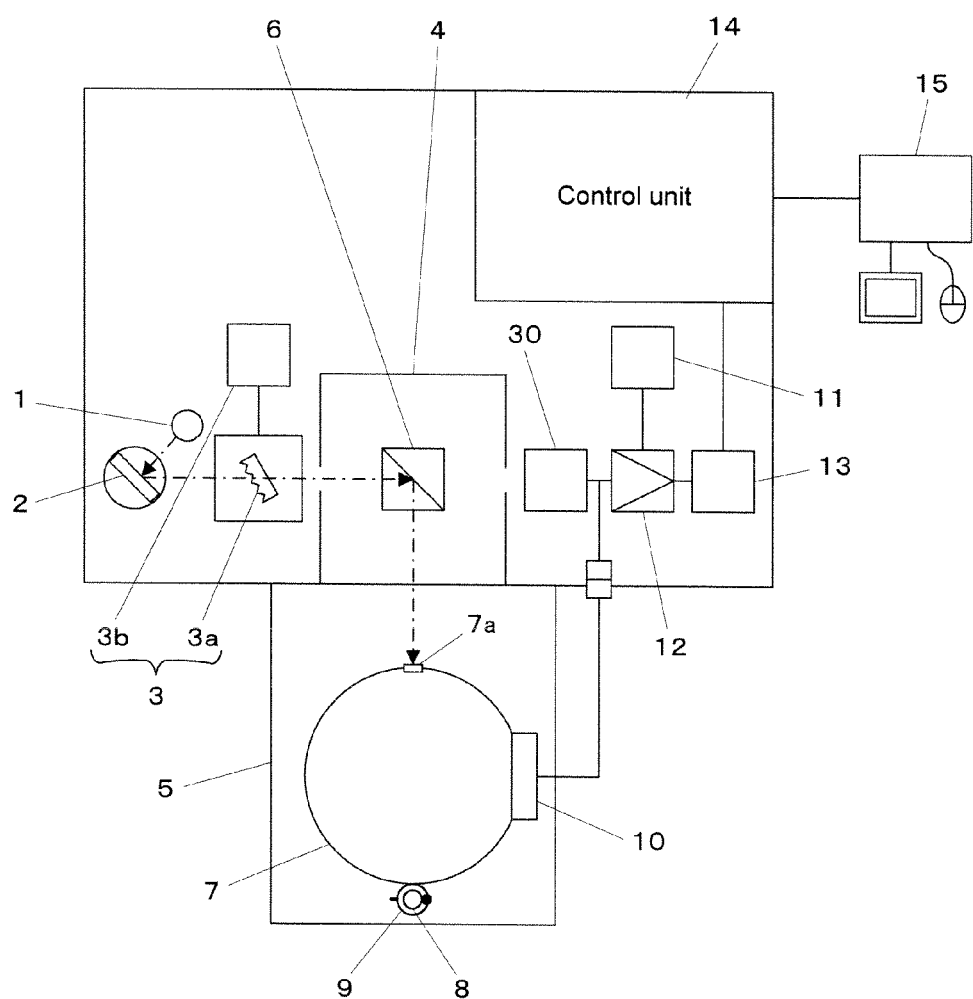
FIG. 2 is a schematic diagram showing the structure according to an embodiment of the present invention.

In the following, the embodiments of the present invention are described in reference to the drawings. FIG. 2 is a schematic diagram showing the structure according to an embodiment.

The basic structure of this embodiment is provided as a general purpose ultraviolet, visible, near-infrared spectrometer equipped with an integrating sphere as an external part, where light from a light source 1 is directed to a spectrometer 3 by a mirror 2 that adjusts the direction of the optical path. The main body of the spectrometer 3 consists of a diffraction grating 3a and a wavelength feeding mechanism 3b for adjusting the angle thereof, and the wavelength of single color light directed to a sample chamber 4 changes by changing the angle of the diffraction grating 3a. That is to say, the wavelength of measurement light led into the sample chamber 4 is selected by the spectrometer 3.

A mirror 6 for directing measurement light, of which the wavelength has been selected by the spectrometer 3, into an externally attached housing 5 is provided within the sample chamber 4. An integrating sphere 7 is provided within the housing 5 so that the measurement light reflected from the mirror 6 enters into the integrating sphere 7 through an opening for guiding measurement light 7a that is provided in the integrating sphere 7, and thus, a sample container 8 is irradiated with the measurement light through an opening for setting a sample for reflection measurement 7b (see FIG. 3) that is provided in the integrating sphere 7.

Figure 3A:
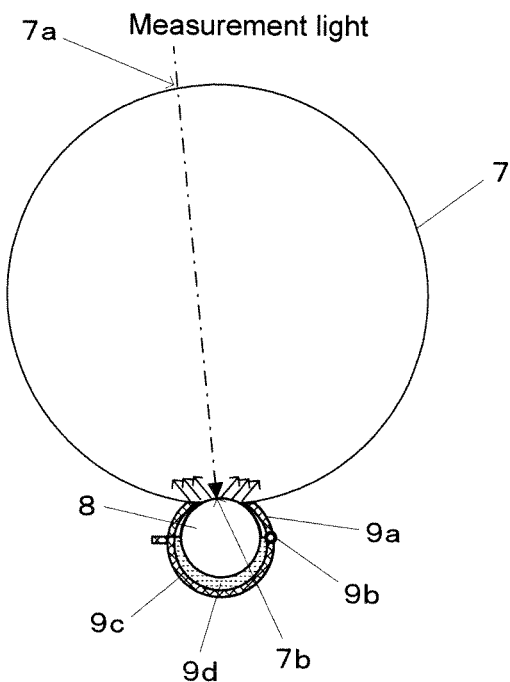
FIG. 3A is a schematic diagram showing the optical path of measurement light inside the integrating sphere, and the state in which a sample container that contains milk to be analyzed is held according to the embodiment of the present invention.

FIG. 3A is a schematic diagram showing the optical path of the measurement light inside the integrating sphere 7 and the state in which the sample container 8 that contains milk to be analyzed is held. At least the opening for guiding measurement light 7a, through which measurement light enters, and the opening for setting a sample for reflection measurement 7b are created in the integrating sphere 7. The sample container 8 that contains milk to be analyzed is positioned and fixed to the outside of the opening for setting a sample for reflection measurement 7b so that a side of this sample container 8 faces the inside of the integrating sphere 7 so as to be irradiated with measurement light. This embodiment adopts total beam reflection measurement, and measurement light enters in the direction that inclines approximately 8° relative to a normal of the sample container 8. Here, it is not necessary for the embodiment to adopt total beam reflection measurement, and diffuse reflection measurement can also be adopted.

The inner surface of the integrating sphere 7 is spherical and made of a light scattering material having high reflectance, such as barium sulfate, and at the same time, a holding mechanism 9 for positioning and fixing the sample container 8 to the integrating sphere 7 under a constant positional relationship is provided outside the integrating sphere 7 in close proximity to the opening for setting a sample for reflection measurement 7b.

Figure 3B:
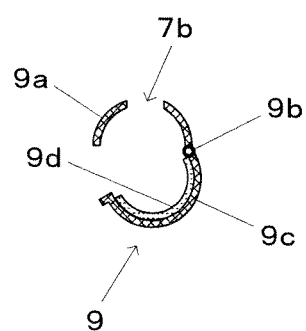
FIG. 3B is a schematic diagram showing the state in which the holding mechanism is open.

This embodiment uses a screw tube in cylindrical form for the sample container 8, and thus, the holding mechanism 9 is approximately in cylindrical form extending in the vertical direction as a whole and is provided with a main body 9a, of which the lower end portion is fixed to the housing 5, and a lid 9c that is supported by the main body 9a via a hinge mechanism 9b so as to be opened and closed freely. FIG. 3B is a schematic diagram showing the holding mechanism 9 in the state where the lid 9c is open. A weak elastic material 9d, such as sponge, is pasted to the inner surface of the lid 9c, and thus, the sample container 8 is pressed against the main body 9a in the state where the lid 9c is closed, and in this state, the sample container 8 is positioned and fixed to the integrating sphere 7 under a constant positional relationship vis-à-vis the opening for setting a sample for reflection measurement 7b.

As shown in FIG. 2, a detector 10 is attached to the integrating sphere 7 in such a location as to be away from both the opening for guiding measurement light 7a and the opening for setting a sample for reflection measurement 7b by approximately 90°. The detector 10 is attached to the integrating sphere 7 so that the sensitive surface of the detector 10 covers the opening created in the integrating sphere 7, and thus, the measurement light reflected from milk within the sample container 8 is reflected and scatters from the inner surface of the integrating sphere 7, and then is condensed so that the intensity of the reflected light is detected. FIG. 3A does not show the detector 10 for the purpose of simplifying the drawing. Though the actual apparatus uses a so-called double-beam system where the inside of the integrating sphere 7 is irradiated with reference light for monitoring the fluctuation of the light source, it is not shown in FIGS. 2 and 3A.

The output from the detector 10 for detecting the reflection light within the integrating sphere 7 is amplified by an amplifier 12, of which the amplification is set to a desired value by a gain setting mechanism 11, and is digitalized by an A/D converter 13 so as to be taken in by a control unit 14.

The control unit 14 stores a program required for controlling the apparatus and information, such as setting the parameters, and controls the entirety of the apparatus. In addition, the detection data of the reflection light to be analyzed is converted to relative reflectance data as compared to the reflectance of the below-described standard sample through calculation by carrying out baseline correction using the standard sample.

The control unit 14 is connected to a personal computer 15, and this personal computer 15 displays the relative reflectance data for each wavelength that has been taken in from the control unit 14, that is to say, the reflection spectrum of the sample, and in addition prepares a measurement model on the basis of an assay technique according to the below-described multivariate analysis and calculates the amount of lipids of the sample to be analyzed from this measurement model and the reflection spectrum to be analyzed so as to display the results.

Here, this embodiment uses a multipurpose spectrometer as the base, and therefore, the mirror 6 for directing the measurement light from the spectrometer 3 towards the integrating sphere 7 is removable in such a manner that a cell holder is attached in place of the mirror 6 in the case where the integrating sphere 7 is not used. The cell holder is to hold a sample cell, and in this case, the measurement light from the spectrometer 3 transmits through the sample cell within the sample chamber 4 so as to be detected by the detector 30, and the output thereof is amplified by the amplifier 12.

Figure 4:
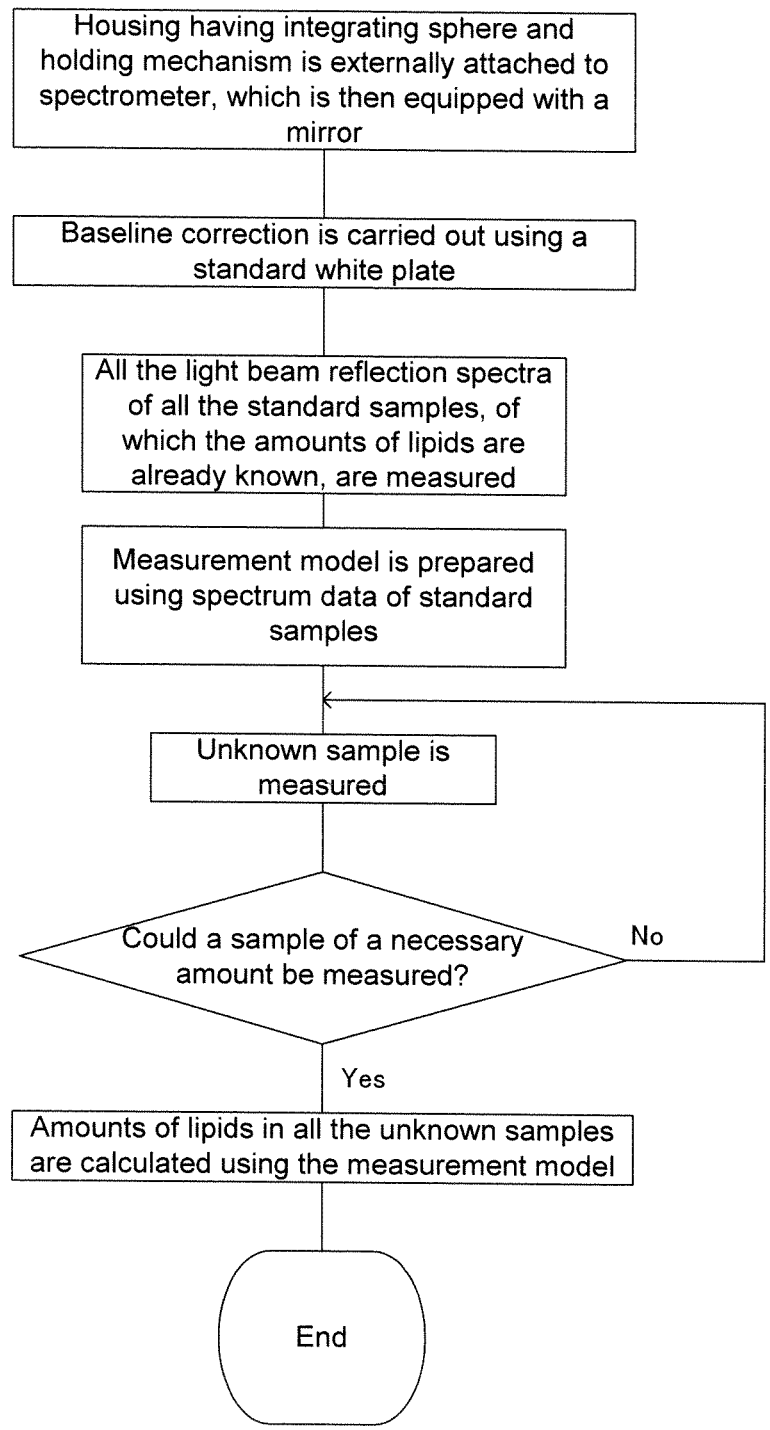
FIG. 4 is a flow chart showing the procedure for measuring the amount of lipids in milk according to the embodiment of the present invention.

The procedure for analyzing the amount of lipids in milk by using the above-described structure according to the embodiment of the present invention is described below. FIG. 4 is a flow chart showing this procedure.

An external housing 5 having an integrating sphere 7 and a holding mechanism 9 for a sample container 8 is attached to a multipurpose spectrometer, which is at the same time engaged with a mirror for changing the optical path 6. After that, a standard white plate, such as a ceramic white plate or a barium sulfate plate, is installed in the opening for setting a sample for reflection measurement 7b in the integrating sphere 7 (see FIG. 3A), and thus, a baseline correction is carried out.

Next, a number of standard samples, of which the amount of lipids is already known, are used in such a manner that each sample is contained in the sample container 8, which is held by the holding mechanism 9, and the reflection spectrum is found sequentially. Then, this spectrum data is used to prepare a measurement model. This measurement model is prepared on the basis of the assay technique of a multivariate analysis, such as multiple regression or PLS. This measurement model is described in detail below.

Next, an unknown sample is contained in the sample container 8, which is then held by the holding mechanism 9 in the same manner as in the above, and the reflection spectrum is measured. Thus, all the samples that are required to be measured are measured, and the amounts of lipids of all the unknown samples are calculated using the measurement model.

The fact that the assay of liquids included in milk is effective when an integrating sphere is used to measure the reflection spectrum of the milk is confirmed by the experiment described below.

Nine types of milk in total: three types of rich milk, three types of regular milk, and three types of low fat milk, which are all available commercially, were prepared. These types of milk are all different from each other, not only in the amount of lipids, but also in the amounts of other components, such as protein and carbohydrates, as shown in Table 1, which shows the amounts of each component. In this situation, the experiment was carried out to see if only the amount of lipids could be measured precisely. Here, Table 1 shows values found on the respective milk packs where the makers measure the amount of lipids in accordance with a Gerber method or a Roese-Gottlieb method. In addition, the amount of lipids slightly varies depending on the season, and the values found on the milk packs are the average values throughout one year.

TABLE 1

| Sample type | Protein (g/200 ml or 200 g) | Lipids (g/200 ml or 200 g) | Carbohydrates (g/200 ml or 200 g) |
|---|---|---|---|
| Rich 1 | 6.6 | 9.3 | 10.0 |
| Rich 2 | 6.4 | 9.5 | 10.7 |
| Rich 3 | 6.6 | 9.4 | 10.3 |
| Regular 1 | 6.5 | 7.6 | 9.6 |
| Regular 2 | 6.4 | 7.6 | 9.6 |
| Regular 3 | 7.2 | 7.8 | 9.4 |
| Low fat 1 | 7.6 | 0.2 | 10.8 |
| Low fat 2 | 7.6 | 2.0 | 11.4 |
| Low fat 3 | 6.0 | 1.0 | 9.2 |

Figure 5:
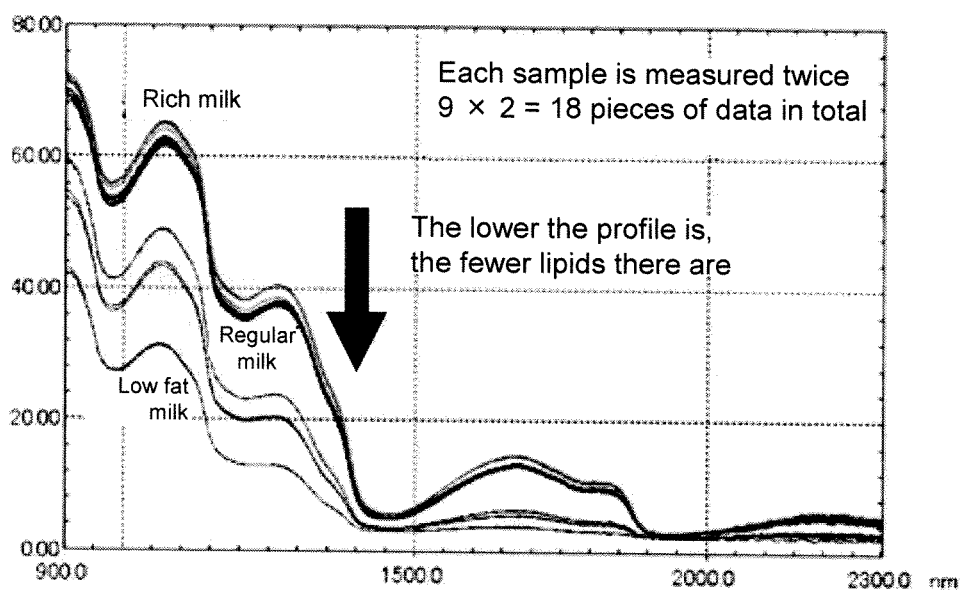
FIG. 5 is a graph showing the results of measurements of the reflection spectra of nine types of milk used for experiments.

Each of the prepared nine types of milk was contained in a sample container, which was a screw tube, and the reflection spectrum was measured two times each. The results are shown in FIG. 5. Judging from FIG. 5 and Table 1, it is possible for the difference in the reflection spectrum to mainly reflect the difference in the amount of lipids, and the lower the amount of lipids is, the lower the value of the reflection spectrum is shown in general.

Sample 1 and Sample 3 of each of the three types of milk from among Rich 1 to 3, Regular 1 to 3, and Low fat 1 to 3 shown in Table 1 were designated as standard samples (12 pieces of data in total), and the reflectance data of the respective reflection spectra was used as description variables, and the amounts of lipids were used as target variables so that measurement models were prepared. The analysis techniques used for the preparation of the measurement models were two techniques, multiple regression and PLS (partial least squares), where the assay precision in the measurement models prepared in accordance with the respective techniques were compared. Here, the data of four wavelengths, 1000 nm, 1200 nm, 1500 nm, and 1800 nm, was used for multiple regression. Meanwhile, all the data of all the wavelengths between 1100 nm and 1500 nm was used for PLS. In addition, the mean values of the data were averaged in PLS.

Next, the remaining Sample 2 of each type of milk from among Rich 1 to 3, Regular 1 to 3, and Low fat 1 to 3 was used as a sample for verification (6 pieces of data in total) so as to verify the measurement models.

Figure 6:
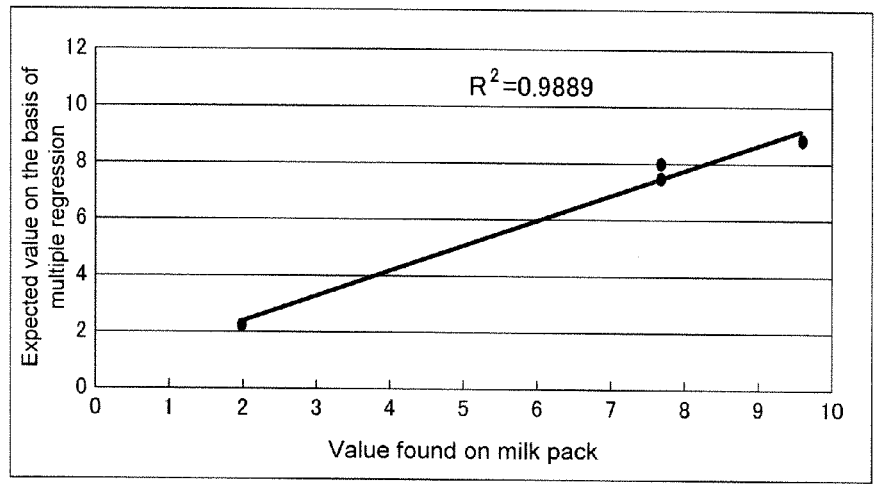
FIG. 6 is a graph showing the mutual relationship between the results expected from a multiple regression measurement model and the actual amount of lipids.
Figure 7:
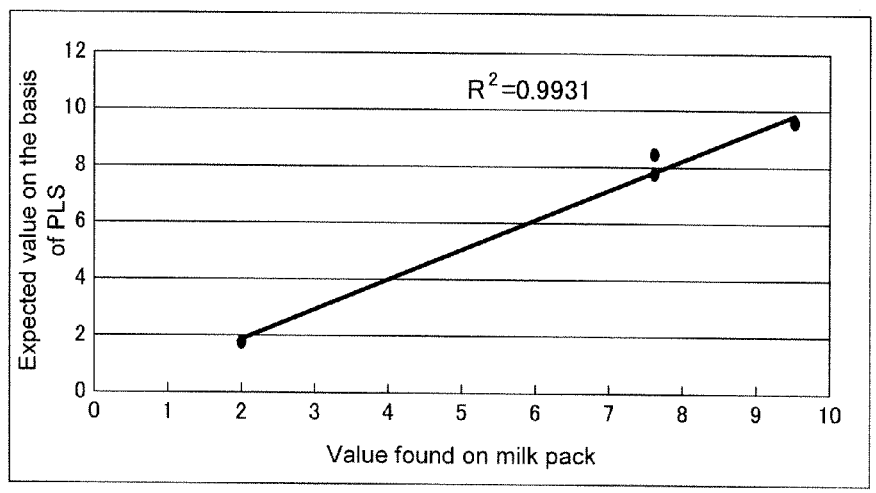
FIG. 7 is a graph showing the mutual relationship between the results expected from a PLS measurement model and the actual amount of lipids.

Table 2 shows the expected amount of lipids of each sample for verification using each measurement model, multiple regression and PLS, and the actual amounts of lipids (amounts of lipids found on the milk packs). FIG. 6 is a graph showing the mutual relationship between the expected values using a measurement model on the basis of multiple regression and the actual amounts of lipids (values found on the packs). FIG. 7 is a graph showing the mutual relationship between the expected values using a measurement model on the basis of PLS and the actual amounts of lipids (values found on the packs).

TABLE 2

| Sample type | Value found on milk pack (g/200 ml or 200 g) | Expected values on the basis of multiple regression | Expected values on the basis of PLS |
|---|---|---|---|
| Rich 2-1 | 9.5 | 8.87 | 9.57 |
| Rich 2-2 | 9.5 | 8.89 | 9.65 |
| Regular 2-1 | 7.6 | 8.04 | 8.40 |
| Regular 2-2 | 7.6 | 7.59 | 7.71 |
| Low fat 2-1 | 2.0 | 2.24 | 1.78 |
| Low fat 2-2 | 2.0 | 2.36 | 1.72 |

As is clear from Table 2 and FIGS. 6 and 7, the two measurement models on the basis of multiple regression and PLS respectively provided good results, and thus, it was confirmed that the method was effective for assaying the amount of lipids using a measurement model prepared in accordance with an assay technique on the basis of the multivariate analysis and the results of reflection measurement of milk by means of a spectrometer equipped with an integrating sphere.

Though assay models were prepared using multiple regression and PLS in the above-described experiment, other assay techniques for multivariate analysis, such as PCR (principle component regression), a kernel method, and support vector regression (SVR), can be used in the same manner.

Though FIG. 2 shows an embodiment where a sample is contained in a screw tube, which is then set to a spectrometer, the container for containing a sample is not particularly limited, and a test tube and a cell made of glass that can be generally used for spectrometry can also be used.

Figure 8:
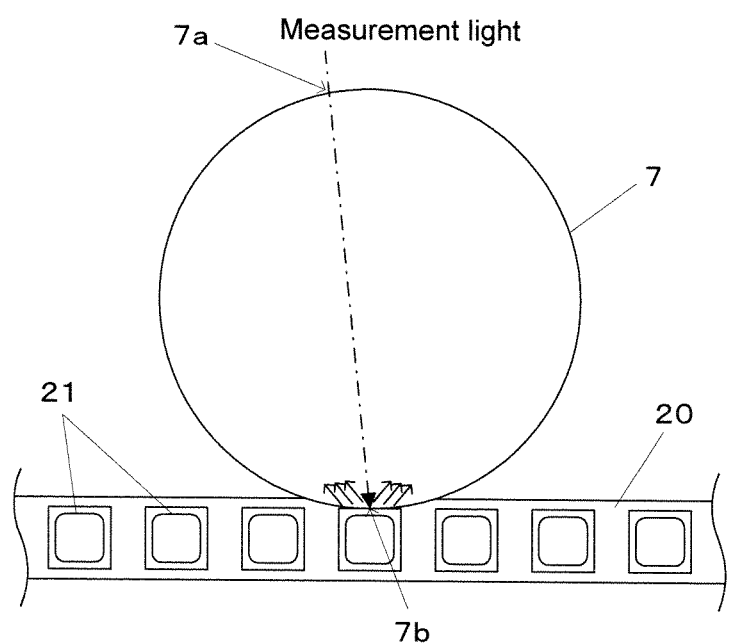
FIG. 8 is a schematic diagram showing the structure of a main portion according to another embodiment of the present invention.

Though FIG. 2 shows an embodiment where an individual sample container is manually set to a spectrometer, online measurement can be carried out in place of this. FIG. 8 shows an example of the structure of its main portion.

In the example in FIG. 8, the measurement system, including the spectrometer and the integrating hemisphere, is the same as in the example in FIG. 2. However, the example in FIG. 8 is different from the example in FIG. 2 in that a supplying mechanism 20 for sequentially supplying sample containers 21 that contain a sample to a close vicinity of the opening for setting a sample for reflection measurement 7b is provided in place of the holding mechanism 9 that is provided outside the opening for setting a sample for reflection measurement 7b in the integrating sphere 7. The supplying mechanism 20 works in sync with the operation for measuring the reflection spectrum of the spectrometer in such a manner as to move the next sample to a predetermined location outside the opening for setting a sample for reflection measurement 7b in the integrating sphere 7 whenever the measurement of one sample has been completed. In this example, milk bins that are commercially distributed can be used as the sample containers 21, which makes it possible to subject milk packed in a milk bin to measurement as is, and thus, online measurement can be realized in a bin packing process at the time of milk production.

Next, a case where the concentration of green vegetable juice was measured using the embodiment in FIG. 2 is described. Green vegetable juice is generally gained by squeezing vegetables, such as barley leaves or kale, and according to the present invention, the concentration of vegetables juice in suspension can be measured.

In this case as well, a screw tube was used as the sample container 8 in the same manner as in the above-described case where milk was subjected to measurement, and 11 types of samples shown in Tables 3 and 4 were prepared by sequentially diluting the green vegetable juice to be analyzed in such a manner that the samples in Table 3 were used as the standard samples, and the samples in Table 4 were used as the samples for verification.

As shown in Table 3, (1) is the original liquid and (11) is pure water from among these samples, where the concentration of each sample is shown as a relative value with the original liquid (1) being 1.0 and pure water (11) being 0.

TABLE 3

| Standard sample | Concentration |
| --- | --- |
| (1) | 1.0 (original liquid) |
| (3) | 0.8 |
| (4) | 0.7 |
| (6) | 0.5 |
| (7) | 0.4 |
| (9) | 0.2 |
| (10) | 0.1 |
| (11) | 0 (pure water) |

TABLE 4

| Sample for verification | Concentration |
| --- | --- |
| (2) | 0.9 |
| (5) | 0.6 |
| (8) | 0.3 |

Figure 9:
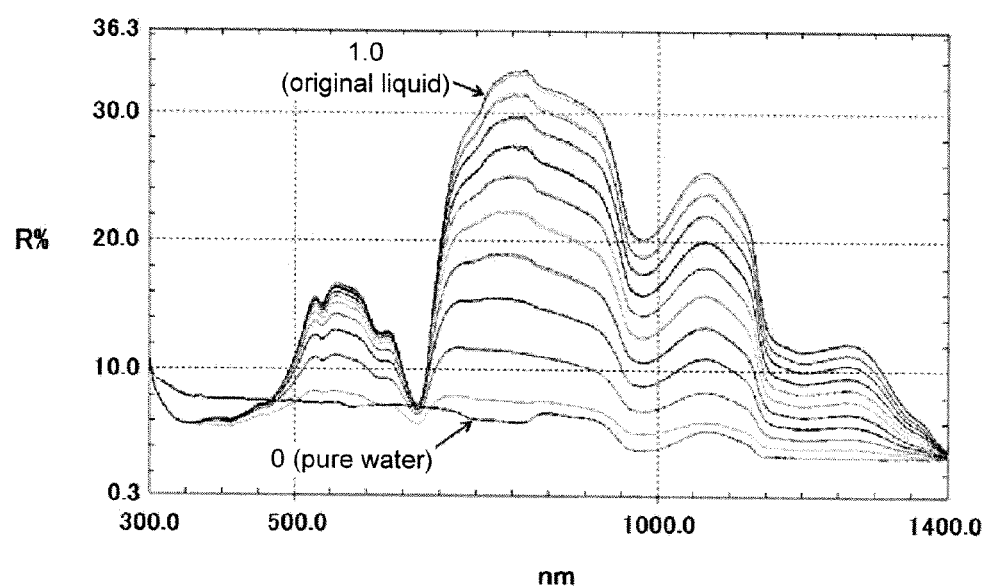
FIG. 9 is a graph showing the results of measurements of the reflection spectra of 11 types of green vegetable juices used for the experiments.

FIG. 9 shows the results of measurement of the reflection spectrum in the apparatus in FIG. 2 where each sample is contained in a screw tube. The reflection spectra in FIG. 9 are placed in the order where the one with a higher concentration has a higher profile or the one with a lower concentration has a lower profile, and thus, it can be seen that the thus-gained reflection spectra relate to the concentration. In addition, the measurement was repeated by replacing the screw tube, and as a result, it was confirmed that the reproducibility was excellent.

As for the measurement models for assay, two types were prepared using the reflection spectrum of each of the eight types of standard samples listed in Table 3. One is simple linear regression, which is an assay using one wavelength in each reflection spectrum, and the other is multiple regression for multivariate analysis, which is an assay using a number of wavelengths in each reflection spectrum. In addition, the assay precision was compared between these two measurement models.

That is to say, the reflection spectrum of each of the three types of samples for verification shown in Table 4 was measured twice, and the concentration was estimated from the six pieces of data in total using the above-described two measurement models respectively. The results are shown in Table 5. In Table 5, RMSEP is the average error between the actual value and the expected value, and the smaller the value thereof is, the better the assay precision is.

TABLE 5

| Sample for verification | Actual concentration | Expected value on the basis of simple linear regression | Expected value on the basis of multiple regression |
| --- | --- | --- | --- |
| (2)-1 | 0.9 | 0.887 | 0.886 |
| (2)-2 | 0.9 | 0.896 | 0.900 |
| (5)-1 | 0.6 | 0.623 | 0.598 |
| (5)-2 | 0.6 | 0.627 | 0.600 |
| (8)-1 | 0.3 | 0.301 | 0.307 |
| (8)-2 | 0.3 | 0.299 | 0.296 |
| RMSEP | — | 0.016 | 0.007 |

Figure 10:
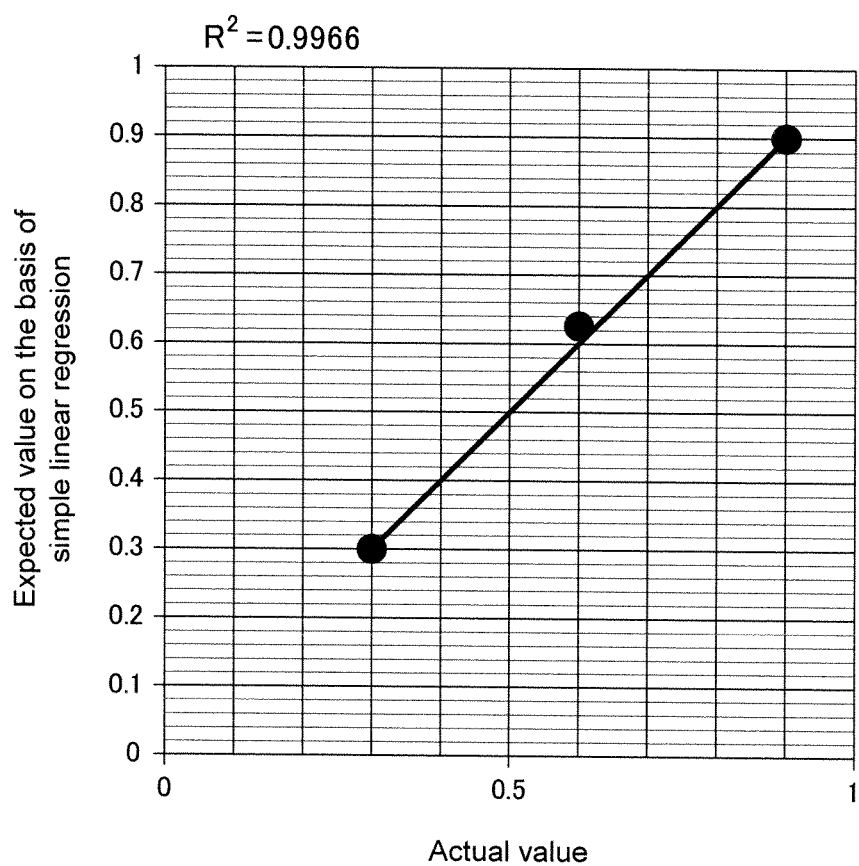
FIG. 10 is a graph showing the mutual relationship between the results expected from a simple linear regression measurement model for the concentration of green vegetable juice and the actual concentration.
Figure 11:
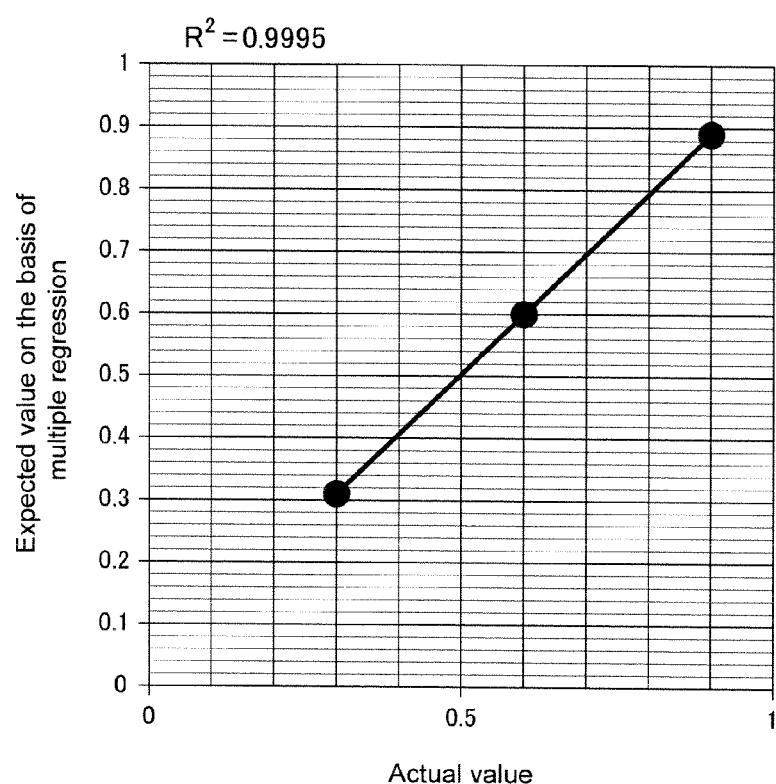
FIG. 11 is a graph showing the mutual relationship between the results expected from a multiple regression measurement model for the concentration of green vegetable juice and the actual concentration.

FIG. 10 is a graph showing the mutual relationship between the expected value using a measurement model on the basis of simple linear regression and the actual concentration, and FIG. 11 is a graph showing the mutual relationship between the expected value using a measurement model on the basis of multiple regression and the actual concentration. It was confirmed from Table 5 and FIGS. 10 and 11 that the assay precision was higher when multiple regression (multivariate analysis) was used to prepare the measurement model. This is consistent with a general argument that the precision is better when multiple regression is used than when single linear regression is used because the reflectance of measurement light and the concentration in suspension are not in a complete proportional relationship (linear relationship).

Next, a case where the concentration of microscopic algae in a suspension was measured is described.

Nannochloropsis liquid (10 billion cells/ml, made by Higashimaru Co., Ltd.) was used as a sample of a microscopic algae suspension to be analyzed. In this case as well, the spectrometer was the same as that according to the embodiment in FIG. 2, and a screw tube was used as a sample container in order to carry out an assay experiment.

The above-described Nannochloropsis liquid was diluted sequentially so as to prepare 12 types of samples, shown in Tables 6 and 7, and the samples in Table 6 were used as the standard samples and the samples in Table 7 were used as the samples for verification.

TABLE 6

| Standard sample | Concentration |
| --- | --- |
| (1) | 1.0 (original liquid) |
| (2) | 0.9 |
| (3) | 0.8 |
| (5) | 0.6 |
| (6) | 0.5 |
| (7) | 0.4 |
| (9) | 0.2 |
| (10) | 0.1 |
| (12) | 0 (pure water) |

TABLE 7

| Sample for verification | Concentration |
| --- | --- |
| (4) | 0.7 |
| (8) | 0.3 |
| (11) | 0.05 |

In this example as well, as shown in Table 6, sample (1) is an original liquid and sample (12) is pure water, and the concentration of each sample is denoted as a relative value when the concentration of the original liquid (1) is 1.0 and the concentration of the pure water (12) is 0.

Figure 12:
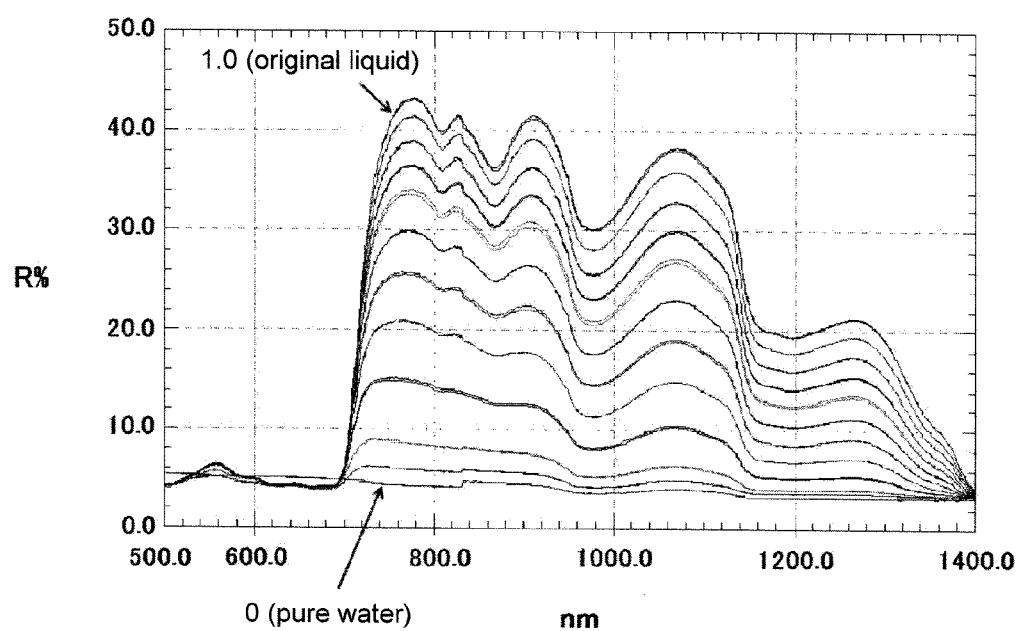
FIG. 12 is a graph showing the results of measurement of the reflection spectra of 12 types of Nannochloropsis (registered trademark) suspensions used for the experiments for measuring the concentrations of microscopic algae in a microscopic alga suspension.

FIG. 12 shows the results of measurement of the reflection spectrum in the apparatus in FIG. 2 where each sample is contained in two screw tubes (12 samples×2=24 pieces of data). The reflection spectra in FIG. 12 are placed in the order where the one with a higher concentration has a higher profile or the one with a lower concentration has a lower profile, and thus, it was confirmed in the liquids where microscopic algae are suspended as well that the thus-gained reflection spectra relate to the concentration. In addition, the measurement was repeated by replacing the screw tube, and as a result, it was confirmed that the reproducibility was excellent.

As for the measurement models for assay, two types were prepared using the reflection spectrum of each of the nine types of standard samples listed in Table 6. One is simple linear regression, which is an assay using one wavelength in each reflection spectrum, and the other is multiple regression for multivariate analysis, which is an assay using a number of wavelengths in each reflection spectrum. Here, the reflectance of the wavelength of 910 nm was adopted for single linear regression, and the reflectance of four wavelengths, 870 nm, 910 nm, 980 nm, and 1070 nm were adopted for multiple regression.

Thus, the concentrations were estimated from the reflectance spectra gained by measuring the two container samples for each of the samples for verification in Table 7 (3 samples×2=6 pieces of data) using each of the above-described two types of measurement models. Table 8 shows the results.

TABLE 8

| Sample for verification | Actual concentration | Expected value on the basis of single linear regression | Expected value on the basis of multiple regression |
| --- | --- | --- | --- |
| (4)-1 | 0.7 | 0.729 | 0.692 |
| (4)-2 | 0.7 | 0.734 | 0.691 |
| (8)-1 | 0.3 | 0.324 | 0.283 |
| (8)-2 | 0.3 | 0.323 | 0.300 |
| (11)-1 | 0.05 | 0.014 | 0.053 |
| (11)-2 | 0.05 | 0.015 | 0.054 |
| RMSEP | — | 0.031 | 0.0087 |

As is clear from Table 8, it was confirmed that the concentration of microscopic algae suspended in a liquid could be precisely assumed using the measurement model on the basis of multiple regression.

Though the amount of lipids in milk, the concentration of green vegetables, and the concentration of microscopic algae suspended in a liquid are described on the basis of the experiment results, the same results can be gained for other suspensions. Suspensions can be generally defined as a solution with turbidity in the case where there are a great number of particles, of which the diameter is in a range from 0.1 μm to several hundreds of μm, in a liquid. The great number of particles having such a dimension allows measurement light to be reflected or scattered from the vicinity of the interface of the solution. According to the present invention, this reflected light is captured and used for assay analysis, and the present invention can be equally applied to the suspensions where particles in the above-described diameter range are suspended in a liquid.

That is to say, the present invention can be applied to the measurements of the concentration of lipids in milk, the green vegetables, and microscopic algae suspended a liquid in addition to drinks with turbidity (of which the degree of transparency is low). As for microscopic algae, microscopic algae that produce oil have been vigorously researched in recent years, and it is necessary in the algae biomass field to know the growth rate of the microscopic algae. Microscopic algae chronologically and constantly increase in the number of cells, and therefore, it is important to know the concentration of the cells at every moment. When the present invention is applied, it is possible to simply measure the concentration thereof. That is to say, assay is possible by simply measuring the reflectance of the several wavelengths used in the measurement model where the time required for the measurement of one sample is approximately one minute. In addition, the present invention is useful for the management of the concentration of a liquid with turbidity in the fields of food production and chemistry.

EXPLANATION OF SYMBOLS

1 Light source
3 Spectrometer
3a Diffraction grating
3b Wavelength feeding mechanism
4 Sample chamber
5 Housing
6 Mirror
7 Integrating sphere
7a Opening for guiding measurement light
7b Opening for setting a sample for reflection measurement
8 Sample container
9 Holding mechanism
9a Main body
9b Hinge mechanism
9c Lid
9d Elastic material
11 Gain setting mechanism
12 Amplifier
13 A/D converter
14 Control unit
15 Personal computer
20 Supplying mechanism
21 Sample container (milk bin)

What is claimed is:

1. A method for analyzing a concentration of one of vegetable juice and microscopic algae in a suspension, the method comprising the steps of:
   using a spectrometer equipped with an integrating sphere;
   gaining a state where a sample container that contains the suspension of the one of vegetable juice and microscopic algae to be analyzed faces an inside of the integrating sphere through an opening of the integrating sphere;
   selecting wavelengths sequentially from a range of measured wavelengths of measurement light;
   irradiating the suspension in the sample container with the measurement light through another opening of the integrating sphere in the state;
   detecting light reflected from the suspension with a detector provided in the integrating sphere so that a reflection spectrum is measured; and
   finding the concentration of the one of vegetable juice and microscopic algae in the suspension to be analyzed from results of the measurement of the reflection spectrum and a measurement model prepared in accordance with an assay technique on the basis of a recursion using respective reflection spectra of a number of types of standard samples, of which concentrations in the suspension are already known, wherein
   the sample container has a thickness to allow reflected light from particles, in the suspension, adjacent to a liquid interface to return to the integrating sphere, while allowing reflected light from particles, in the suspension, distant from the liquid interface not to return to the integrating sphere.

2. The method according to claim 1, wherein the assay technique on the basis of the recursion is an assay technique on the basis of a multivariate analysis.

3. The method according to claim 1, wherein a container, which can be distributed, for containing a suspension to be analyzed is used as the sample container, and the suspension to be analyzed is subjected to analysis in a distribution state where the suspension is sealed in the container.

\* \* \* \* \*